United States Patent
Williams

(12) 
(10) Patent No.: US 6,592,892 B1
(45) Date of Patent: Jul. 15, 2003

(54) FLUSHABLE DISPOSABLE POLYMERIC PRODUCTS

(75) Inventor: Simon F. Williams, Sherborn, MA (US)

(73) Assignee: Tepha, Inc., Cambridge, MA (US)

( * ) Notice: Subject to any disclaimer, the term of this patent is extended or adjusted under 35 U.S.C. 154(b) by 0 days.

(21) Appl. No.: 09/649,978

(22) Filed: Aug. 29, 2000

Related U.S. Application Data
(60) Provisional application No. 60/151,509, filed on Aug. 30, 1999.

(51) Int. Cl.$^7$ .......................... A61K 9/70; A61F 13/02; A61F 13/00
(52) U.S. Cl. ................ 424/449; 424/78.02; 424/78.08; 424/448
(58) Field of Search ............................... 424/448, 449, 424/78.02, 78.08

(56) References Cited

U.S. PATENT DOCUMENTS

| | | | |
|---|---|---|---|
| 3,598,122 | A | 8/1971 | Zaffaroni et al. |
| 3,598,123 | A | 8/1971 | Zaffaroni et al. |
| 3,731,683 | A | 5/1973 | Zaffaroni |
| 3,797,494 | A | 3/1974 | Zaffaroni |
| 4,031,894 | A | 6/1977 | Urquhart et al. |
| 4,201,211 | A | 5/1980 | Chandrasekaran et al. |
| 4,286,592 | A | 9/1981 | Chandrasekaran |
| 4,314,557 | A | 2/1982 | Chandrasekaran |
| 4,379,454 | A | 4/1983 | Campbell et al. |
| 4,435,180 | A | 3/1984 | Leeper |
| 4,559,222 | A | 12/1985 | Enscore et al. |
| 4,573,995 | A | 3/1986 | Chen et al. |
| 4,588,580 | A | 5/1986 | Gale et al. |
| 4,603,070 | A | 7/1986 | Steel et al. |
| 4,645,502 | A | 2/1987 | Gale et al. |
| 4,704,282 | A | 11/1987 | Campbell et al. |
| 4,788,062 | A | 11/1988 | Gale et al. |
| 4,816,258 | A | 3/1989 | Nedberge et al. |
| 4,849,226 | A | 7/1989 | Gale |
| 4,856,188 | A | 8/1989 | Sibalis |
| 4,908,027 | A | 3/1990 | Enscore et al. |
| 4,943,435 | A | 7/1990 | Baker et al. |
| 5,502,116 | A | 3/1996 | Noda |
| 5,563,239 | A | 10/1996 | Hubbs et al. |
| 5,614,576 | A | 3/1997 | Rutherford et al. |
| 5,753,364 | A | 5/1998 | Rutherford et al. |
| 5,814,599 | A | 9/1998 | Mitragotri et al. |
| 5,879,322 | A | 3/1999 | Lattin et al. |
| 5,919,478 | A | 7/1999 | Landrau et al. |
| 6,056,970 | A | * 5/2000 | Greenawalt et al. ........ 424/426 |
| 6,119,567 | A | * 9/2000 | Schindler et al. .............. 83/171 |

FOREIGN PATENT DOCUMENTS

| | | |
|---|---|---|
| CA | 2 259 098 | 7/1999 |
| GB | 2 166 354 A | 5/1986 |
| WO | WO 95/02649 A1 | 1/1995 |
| WO | WO 98/51812 A2 | 11/1998 |
| WO | WO 99/32536 A1 | 7/1999 |

OTHER PUBLICATIONS

Agostini, et al., "Synthesis and Characterization of Poly–β–Hydroxybutyrate. I. Synthesis of Crystalline DL Poly–β–Hydroxybutyrate from DL–β–Butyrolactone, "*Polym. Sci.* Part A–1, 9:2775–2787 (1971).

Byrom, "Miscellaneous Biomaterials," in *Biomaterials* (D. Byrom, ed.) pp. 333–359 (MacMillan Publishers, London 1991).

De Smet, et al., "Characterization of intracellular inclusions formed by Pseudomonas oleovorans during growth on octane," *J. Bacteriol.* 154:870–78 (1983).

Dubois, et al., "Macromolecular Engineering of Polylactones and Polylactides. 12. Study of the Depolymerization Reactions of Poly (ε–caprolactone) with Functional Aluminum Alkoxide End Groups," *Macromolecules* 26:4407–12 (1993).

Gross, et al., "Polymerization if β–monosubstituted–b–propiolactones using trialkylaminimum–water catalytic systems and polymer characterization," *Macromolecules* 21:2657–2668 (1988).

Hocking & Marchessault, "Syndiotactic poly[(R, S)–β–hydroxybutyrate] isolated from methylaluminoxane–catalyzed polymerization," *Polym. Bull.* 30:163–170 (1993).

Hocking & Marchessault, "Biopolyesters" Griffin, Ed., "Chemistry and Technology of Biodegradable Polymers," pp. 48–96 (Chapman and Hall, London, 1994).

Holmes, "Biologically Produced (R)–3–hydroxyalkanoate Polymers and Copolymers," in Bassett Ed., "Developments in Crystalline Polymers," pp. 1–65 (Elsevier, London, vol. 2, , 1988).

Hori, et al., "Ring–Opening Copolymerization of Optically Active β–Butyrolactone with Several Lactones Catalyzed by Distannoxane Complexes: Synthesis of New Biodegradable Polyesters," *Macromolecules* 26:4388–4390 (1993).

Hori, et al., "Ring–Opening Polymerization of Optically Active β–Butyrolactone Using Distannoxane Catalysts: Synthesis of High Molecular Wright Poly(3–hydroxybutyrate)," *Macromolecules* 26:5533–5534 (1993).

Kemnitzer, et al., "Preparation of predominantly Syndiotactic Poly(β–hydroxybutyrate) by the Tributylin Methoxide Catalyzed Ring–Opening Polymerization of racemic β–Butyrolactone," *Macromolecules* 26:1221–1229 (1993).

(List continued on next page.)

*Primary Examiner*—Shelley A. Dodson
(74) *Attorney, Agent, or Firm*—Holland & Knight LLP

(57) ABSTRACT

Materials suitable for preparing components of flushable drug delivery systems are described. These components include drug impermeable and drug permeable materials, including materials that can be used to control the rate of release of drugs from the device, and pressure sensitive adhesive compositions which are drug compatible. Methods for fabricating these devices, including transdermal drug delivery patches, are described.

28 Claims, No Drawings

OTHER PUBLICATIONS

Koosha, "Preparation and characterization of biodegradable polymeric drug carriers," Ph.D. Dissertation, 1989, Univ. Nottingham, UK., *Diss. Abstr. Int. B* 51:1206 (1990).

Lafferty et al., "Microbial Production of Poly–β–hydroxybutyric acid," Rehm and Reed, Eds., "Biotechnology" Verlagsgesellschaft, Weinheim, vol. 66, 1988, pp. 135–176.

Le Borgne & Spassky, "Stereoelective polymerization of β–butyrolactone," *Polymer* 30:2312–2319 (1989).

Lemoigne and Roukhelman, "Fermetation β–Hydroxybutyrique Caracterisation et Evolution Des Produits de Deshydration et de Polymerisation de L'acide β–Dehydroxybutyrique," *Annales des fermentations*, 5:527–36 (1925).

Madison & Huisman, "Metabolic engineering of poly(3–hydroxyalkanoates): from DNA to plastic," *Microbiol. Mol. Biol. Rev.* 63:21–53 (1999).

Müller & Seebach, "Poly(hydroxyalkanoates): A Fifth Class of Physiologically Important Organic Biopolymers," *Angew. Chem. Int. Ed. Engl.* 32:477–502 (1993).

Poutin & Akhtar, "Biosynthetic polyhydroxyalkanoates and their potential in drug delivery," *Advanced Drug Delivery Reviews* 18:133–162 (1996).

Steinbüchel, et al., "A Pseudomonas strain accumulating polyesters of 3–hydroxybutyric acid and medium–chain–length 3–hydroxyalkanoic acids," *Appl. Microbiol. Biotechnol.* 37:691–97 (1992).

Steinbüchel, "Polyhydroxyalkanoic Acids," in Byrom Ed., "Biomaterials" MacMillan Publishers, London, 1991, pp. 123–213.

Tanahashi & Doi, "Thermal Properties and Stereoregularity of Poly(3–hydroxybutyrate) Prepared from optically Active β–Butyrolactone with a Zinc–Based Catalyst," *Macromolecules* 24:5732–5733 (1991).

Wallen and Rohwedder, "Poly–β–hydroxyalakaonate from Activated Sludge," *Environ. Sci. Technol.* 8:576–79 (1974).

Williams & Peoples, "Biodegradable plastics from plants," *CHEMTECH* 26:38–44 (1966).

Williams & Peoples, "Making Plastics Green," *Chem. Br.* 33:29–32 (1997).

Williams, et. al., "PHA applications: addressing the price performance issue I. Tissue engineering," *Int. J. Biol. Macromol.* 25:111–121 (1999).

Xie, et al., "Ring–opening Polymerization of β–butyrolactone by Thermophilic Lipases," *Macromolecules* 30:6997–6998 (1997).

* cited by examiner

FLUSHABLE DISPOSABLE POLYMERIC PRODUCTS

This application claims priority to U.S. Ser. No. 60/151,509 filed Aug. 30, 1999.

FIELD OF THE INVENTION

The present invention generally relates to drug delivery systems and other polymeric products that they can be disposed of after use by flushing into a toilet.

BACKGROUND OF THE INVENTION

Transdermal drug delivery systems are now commonly used to deliver a variety of types of drugs across the skin. Transdermal delivery systems are particularly useful for the delivery of drugs with low molecular weights and high water solubility, and offer some advantages over other delivery systems. For example, these systems deliver drugs directly to the systemic circulation, by-passing problems sometimes associated with first pass metabolism. The systems are also useful for delivering drugs in a steady-state manner, without producing highs and lows in blood levels, and for providing prolonged delivery times. Examples of transdermal drug delivery systems include formulations designed to deliver anti-anginal glyceryl trinitrate (nitroglycerin), formulations designed to deliver nicotine for smoking cessation, and formulations for hormone replacement therapy (HRT) to treat menopausal symptoms and prophylaxis of osteoporosis. These products are sold under tradenames such as DEPONIT™, DUROGESIC™, ESTRACOMBI™, ESTRADERM™, ESTRAPAK™, EVOREL-PAK™, EVOREL™, FEMATRIX™, MINITRON™, NICONIL™, NICORETTE™, NICOTINEL™L, NITRO-DUR™, NITROLINGAL™, SCOPODERM™, and TRANSIDERM-NITROR™.

The initial transdermal patches used one of three approaches to deliver drugs: membrane permeation, multilaminate adhesive dispersion and matrix dispersion. In all three cases the physical appearance of the dosage form resembles an adhesive plaster dressing. The difference in the delivery approach lies in the technique used to retain the drug and control its release. In the membrane permeation approach, a flat packet made with one wall of a drug-impermeable laminate and a second wall made from a rate-controlling membrane is used to hold a reservoir of drug. The membrane is coated externally with a pressure sensitive adhesive polymer which is drug compatible. In the second approach, the drug is contained in an adhesive polymer and is sandwiched between a drug-impermeable backing support and thin layers of rate-controlling adhesive forming a multilaminate adhesive dispersion. In the matrix diffusion approach, the drug is homogeneously dispersed in a matrix molded in a disc of predefined surface area and thickness.

Improvements in the use of transdermal systems continue to be made, for example, with the use of skin penetration enhancers, electrotransport, as well as systems to deliver different drug types, such as insulin for diabetics, and prostaglandins for treatment of peripheral arterial occlusive disease.

One disadvantage to the use of transdermal drug delivery patches relates to the potential hazards associated with their disposal after use. At the end of their use these transdermal drug delivery patches must be safely discarded. This can be a particular concern if no suitable collection system exists and the patch contains residual active ingredients and/or has become contaminated during use, for example, with bodily fluids. The problem is further compounded by the frequency of use of these patches. Many patches, for example, are applied daily for prolonged periods of time. There is also a further complication involved in disposing of those devices which incorporate electrotransport systems, for example, as described in U.S. Pat. No. 5,879,322 to Lattin, et al.

A potentially good method for disposing of transdermal drug delivery patches (and other drug contaminated devices, including simplier devices such as BAND-AID™ plastic adhesive bandages) in a safe and environmentally acceptable manner could involve flushing these patches down the toilet after use. Unfortunately, while the physical and chemical properties of the components of the current transdermal drug delivery vehicles make them well suited to their task of drug delivery, these components are generally derived from materials which will not degrade in water or sewage. Such disposal could lead to blockages in the sewerage system or subsequent contamination.

It is therefore desirable to have flushable transdermal drug delivery systems which are easier to use and can be disposed of in a safe and environmentally acceptable manner. It is also desirable to have other types of flushable drug delivery systems for the same reasons, including systems used for buccal, vaginal and ophthalmic delivery of drugs, as well as adhesive bandages and coverings.

It is therefore an object of this invention to provide components for preparing flushable drug delivery systems and adhesive bandages.

It is a further object of this invention to provide methods for fabricating flushable drug delivery systems and bandages.

SUMMARY OF THE INVENTION

Biodegradable polyhydroxyalkanoate materials suitable for preparing components of flushable drug delivery systems and bandages are described. These components include drug impermeable and drug permeable materials, including materials that can be used to control the rate of release of drugs from the device, and pressure sensitive adhesive compositions which are drug and/or skin compatible. Methods for fabricating these devices, including transdermal drug delivery patches, are described.

DETAILED DESCRIPTION OF THE INVENTION

Materials for Making Flushable Drug Delivery Systems and Bandages

Materials are described which can be used to prepare components of flushable drug delivery systems and bandages, including the plastic laminates, components of the adhesives, moisture and/or drug barriers, and packaging. These materials will break down in sewage to harmless metabolites. In a preferred embodiment the materials are selected from a group of polymers known as polyhydroxyalkanoates. In another preferred embodiment, the material components can be fabricated alone, or with other components and materials, into flushable transdermal, buccal, vaginal, or opthalmic drug delivery devices.

A. Polymers

The systems are formed of compositions that are able to break down in an aqueous environment or in sewage to harmless metabolites. In a preferred form, it is desirable for the materials to have a good shelf-life, degrading only after prolonged contact with water or within one year of discharge into the sewage system, preferably within six months of discharge. A particularly preferred class of materials are polyhydroxyalkanoates.

Polyhydroxyalkanoates (PHAs) are a class of naturally occurring polyesters that are synthesized by numerous organisms in response to environmental stress. For reviews, see Byrom, D., "Miscellaneous Biomaterials," in D. Byrom, Ed., "Biomaterials" MacMillan Publishers, London, 1991, pp. 333–359; Hocking, P. J. and Marchessault, R. H. "Biopolyesters", G. J. L. Griffin, Ed., "Chemistry and Technology of Biodegradable Polymers," Chapman and Hall, London, 1994, pp.48–96; Holmes, P. A., "Biologically Produced (R)-3-hydroxyalkanoate Polymers and Copolymers," in D. C. Bassett Ed., "Developments in Crystalline Polymers," Elsevier, London, Vol. 2, 1988, pp. 1–65; Lafferty et al., "Microbial Production of Poly-β-hydroxybutyric acid," H. J. Rehm and G. Reed, Eds., "Biotechnology", Verlagsgesellschaft, Weinheim, Vol. 66, 1988, pp. 135–176; Müller and Seebach, Angew. Chem. Int. Ed. Engl. 32:477–502 (1993); Steinbüchel, A. "Polyhydroxyalkanoic Acids," in D. Byrom Ed., "Biomaterials", MacMillan Publishers, London, 1991, pp. 123–213; and, Williams and Peoples, CHEMTECH, 26:38–44, (1996).

The PHA biopolymers may be broadly divided into three groups according to the length of their pendant groups and their respective biosynthetic pathways. Those with short pendant groups, such as polyhydroxybutyrate (PHB), a homopolymer of R-3-hydroxybutyric acid (R-3HB) units, are highly crystalline thermoplastic materials, and have been known the longest (Lemoigne, M. and Roukhelman, N., Annales desfermentations, 5:527–536 (1925)). A second group of PHAs containing the short R-3HB units randomly polymerized with much longer pendant group hydroxy acid units were first reported in the early seventies (Wallen, L.L. and Rohwedder, W. K., Environ. Sci. Technol., 8:576–579 (1974)). A number of microorganisms which specifically produce copolymers of R-3HB with these longer pendant group hydroxy acid units are also known and belong to this second group (Steinbüchel, A. and Wiese, S., Appl. Microbiol. Biotechnol., 37:691–697 (1992)). In the early eighties, a research group in The Netherlands identified a third group of PHAs, which contained predominantly longer pendant group hydroxy acids (De Smet, M. J. et al., J. Bacteriol., 154:870–878 (1983)).

The PHA polymers may constitute up to 90% of the dry cell weight of bacteria, and are found as discrete granules inside the bacterial cells. These PHA granules accumulate in response to nutrient limitation and serve as carbon and energy reserve materials. Distinct pathways are used by microorganisms to produce each group of these polymers. One of these pathways leading to the short pendant group polyhydroxyalkanoates (SPGPHAs) involves three enzymes, beta ketothiolase, Acetoacetyl CoA reductase and PHB synthase (sometimes called polymerase). Using this pathway, the homopolymer PHB is synthesized by condensation of two molecules of acetyl-Coenzyme A to give acetoacetyl-Coenzyme A, followed by reduction of this intermediate to R-3-hydroxybutyryl-Coenzyme A, and subsequent polymerization. The last enzyme in this pathway, namely the synthase, has a substrate specificity that can accommodate C3–C5 monomeric units including R-4-hydroxy acid and R-5-hydroxy acid units. This biosynthetic pathway is found, for example, in the bacteria Zoogloea ramigera and Alcaligenes eutrophus.

The biosynthetic pathway which is used to make the third group of PHAs, namely the long pendant group polyhydroxyalkanoates (LPGPHAs), is still partly unknown, however, it is currently thought that the monomeric hydroxyacyl units leading to the LPGPHAs are derived by the β-oxidation of fatty acids and the fatty acid pathway. The R-3-hydroxyacyl-Coenzyme substrates resulting from these routes are then polymerized by PHA synthases (sometimes called polymerases) that have substrate specificities favoring the larger monomeric units in the C6–C14 range. Long pendant group PHAs are produced, for example, by Pseudomonads.

Presumably, the second group of PHAs containing both short R-3HB units and longer pendant group monomers utilize both the pathways described above to provide the hydroxy acid monomers. The latter are then polymerized by PHA synthases able to accept these units.

In all, about 100 different types of hydroxy acids have been incorporated into PHAs by fermentation methods (Williams, S. F. et. al., Int. J. Biol. Macromol., 25:111–121 (1999)). Notably, these include PHAs containing functionalized pendant groups such as esters, double bonds, alkoxy, aromatic, halogens and hydroxy groups.

During the mid-1980's, several research groups were actively identifying and isolating the genes and gene products responsible for PHA synthesis. These efforts have lead to the development of transgenic systems for production of PHAs in both microorganism and plants, as well as enzymatic methods for PHA synthesis. Such routes increase further the available PHA types. These advances have been reviewed in Williams, S. F. and Peoples, O. P., CHEMTECH, 26, 38–44 (1996), Madison, L. L and Huisman, G. W. Microbiol. Mol. Biol. Rev., 63:21–53 (1999), and Williams S. F. and Peoples, O. P., Chem. Br. 33, 29–32 (1997).

In addition to using biological routes for PHA synthesis, PHA polymers may also be derived by chemical synthesis. One widely used approach involves the ring-opening polymerization of β-lactone monomers using various catalysts or initiators such as aluminoxanes, distannoxanes, or alkoxy-zinc and alkoxy-aluminum compounds (see Agostini, D. E. et al., Polym. Sci., Part A-1, 9:2775–2787 (1971); Gross, R. A. et al., Macromolecules, 21:2657–2668 (1988); Dubois, P. I. et al., Macromolecules, 26:4407–4412 (1993); Le Borgne, A. and Spassky, N., Polymer, 30:2312–2319 (1989); Tanahashi, N. and Doi, Y., Macromolecules, 24:5732–5733 (1991); Hori, Y. M. et al., Macromolecules, 26:4388–4390 (1993); Kemnitzer, J. E. et al., Macromolecules, 26:1221–1229 (1993); Hori, Y. M. et al., Macromolecules, 26:5533–5534 (1993); Hocking, P. J. and Marchessault, R. H., Polym. Bull., 30:163–170 (1993). A second approach involves condensation polymerization of esters and is described in U.S. Pat. No. 5,563,239 to Hubbs, J. C. and Harrison, M. N., and references therein. Researchers have also developed chemo-enzymatic methods to prepare PHAs. Xie et al., Macromolecules, 30:6997–6998 (1997), for example, have reported a ring opening polymerization of beta-butyrolactone by thermophilic lipases to yield PHB.

One of the most useful properties of PHAs which readily distinguishes them from petrochemical derived polymers is their biodegradability. Produced naturally by soil bacteria, the PHAs are degraded upon subsequent exposure to these same bacteria in either sewage, soil, compost, or marine sediment.

Biodegradation of PHAs is dependent upon a number of factors such as the composition of the PHA, microbial activity of the environment and the surface area of the item. In addition, temperature, pH, molecular weight and crystallinity are important factors. The rate of biodegradation can be controlled by tailoring the composition of the PHA as well as using additives and chemical treatments. Biodegradation starts when microorganisms begin growing on the surface of the plastic and secrete enzymes which break down the polymer into hydroxy acid monomeric units. The hydroxy acids are then taken up by the microorganisms and used as carbon sources for growth. In aerobic environments the polymers are degraded to carbon dioxide and water, whereas in anaerobic environments the degradation products are carbon dioxide and methane (Williams, S. F. and Peoples, O. P., CHEMTECH, 26, 38–44 (1996)).

Importantly for use in these drug delivery systems, the PHA polymers have fairly good resistance to water and do not dissolve readily upon contact with water. Only after prolonged exposure, normally to highly basic or acidic aqueous solutions, or in active microbial populations, will these materials break down. It is therefore possible to fabricate drug delivery device components from these polymers that are not only resistant or stable to contact with water, but can also provide moisture vapor and water barrier properties to the device. One wearing such a device prepared from outer components comprising these materials would therefore be able to wash and bathe without damaging the device, yet the device can be flushed after use and ultimately degrade. If desired the device could also incorporate a biocide.

The water and moisture barrier properties of the PHA polymers can also be beneficial in designing a controlled release device, particularly when it is desirable to protect an active ingredient from water, regulate its exposure to water, and control the rates of release of the active ingredient(s). Multiple barriers can be used to create a device which is "breathable" yet which contains and protects the active ingredient to be delivered.

For medical or veterinary use, the PHA polymers may be sterilized by gamma irradiation or by using ethylene oxide. Certain PHA polymers may also be sterilized in an autoclave with steam.

B. Additives and Chemical Modifiers of the Polymers

A variety of additives can be incorporated into the PHA polymers to improve the properties of the materials. For example, processibility, mechanical, physical, and chemical properties may all be tailored with the use of additives. Colorants may also be added. It is also possible to chemically and physically modify the PHA polymers to optimize their properties for use (and even to covalently attach active ingredients). The polymers can be surface modified with gas plasma and also crosslinked.

C. Other Polymeric Materials

The polyhydroxyalkanoates as a class of polymers offer a wide range of mechanical properties from semi-crystalline thermoplastics to more elastomeric materials. This range of properties is made possible by the ability to prepare the polymers with different types and ratios of monomers (Williams, S. F. and Peoples, O. P., CHEMTECH, 26:38–44 (1996)), and Doi, Y., "Microbial Polyesters," VCH Publishers, New York, 1990. It is therefore possible not only to produce PHA materials with mechanical properties similar to those currently used in transdermal patches, but also to expand the range of available mechanical properties.

In addition to the polyhydroxyalkanoates, other materials may be used either alone, with another suitable material, or as blends, to prepare components of flushable drug delivery systems. Suitable materials include for example other polyesters derived from either hydroxy acid units or combinations of diols and diacids. Examples include polymers derived from glycolide, lactide, caprolactone, trimethylene carbonates, succinic acid, glycols, 1,4-butanediol, 1,5-pentanediol, 1,6-hexanediol, 1,3-propanediol, and, dioxanone. Other suitable materials include, but are not limited to certain polyurethanes, polyorthoesters, polyanhydrides, polyvinylacetate, cellulose acetate, polycarbonates, polysaccharides, polyamino acids, polyethylene oxide, and polyvinylalcohol.

D. Materials to be Delivered

The polyhydroxyalkanoates are generally available in two physical forms, namely a latex form (Koosha, F. Ph.D. Dissertation, 1989, Univ. Nottingham, UK., Diss. Abstr. Int. B 51:1206 (1990)), and as a dry powder. In the latex form, the PHAs can be used to fabricate a device using aqueous and emulsion processing techniques, whereas the dry powder can be used, for example, in conventional processing techniques, for example, using a solvent or by melt processing.

The PHAs can be encapsulated, be mixed with, or be ionically or covalently coupled to any of a variety of therapeutic, prophylactic or diagnostic agents, either for delivery to a site by the polyhydroxyalkanoate, or to impart properties to the polymer, such as bioadhesion, cell attachment, enhancement of cell growth, inhibition of bacterial growth, and prevention of clot formation.

Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Compounds with a wide range of molecular weight can be encapsulated, for example, between 100 and 500,000 grams or more per mole. Examples of suitable materials include proteins such as antibodies, receptor ligands, and enzymes, peptides such as adhesion peptides, saccharides and polysaccharides, synthetic organic or inorganic drugs, and nucleic acids. Examples of materials which can be encapsulated include enzymes, blood clotting factors, inhibitors or clot dissolving agents such as streptokinase and tissue plasminogen activator; antigens for immunization; hormones and growth factors; polysaccharides such as heparin; oligonucleotides such as antisense oligonucleotides and ribozymes and retroviral vectors for use in gene therapy. The polymer can also be used to encapsulate cells and tissues. Representative diagnostic agents are agents detectable by x-ray, fluorescence, magnetic resonance imaging, radioactivity, ultrasound, computer tomagraphy (CT) and positron emission tomagraphy (PET). Ultrasound diagnostic agents are typically a gas such as air, oxygen or perfluorocarbons.

For controlled release, a wide range of different bioactive compounds can be incorporated into the device. These include hydrophobic, hydrophilic, and high molecular weight macromolecules such as proteins. These bioactive compounds may either be covalently or non-covalently incorporated. The release profile may be adjusted by altering one or more of the following parameters: the nature of the PHA; the properties of the bioactive compound; the physical nature of the drug; and the nature of the device. The phrase "nature of the PHA" is used herein to mean, for example, the composition, structure, and molecular weight of the polymer or polymer mixture, including crosslinking and crystallinity. The phrase "properties of the compound" is used herein to mean, for example, the molecular weight, hydrophobicity and hydrophilicity. The phrase "physical nature of the compound" is used herein to mean, for example, the particle size and the loading of the compound.

The bioactive compound is typically incorporated into the PHAs in a percent loading of between 0.1% and 70% by weight, more preferably between 5% and 50% by weight. The phrase "nature of the device" refers to the device's physical shape, thickness, and form, which may be controlled by the fabrication technique.

E. Bioactive Additives

Other agents may be added to the devices to increase the safety and efficacy of the device. Such agents include but are not limited to compounds with anti-microbial activity, surfactants, steroids, lipids, enzymes, antibodies, fragrances, hormones, anesthetics, and agents enhancing skin penetration.

Methods of Fabricating Flushable Drug Delivery Systems and Components

The materials may be fabricated into flushable drug delivery systems or components thereof using a wide range of processing techniques. Preferred methods of fabricating these systems from the materials include: solvent casting; foaming; leaching; aqueous processing of latex; melt processing, including extrusion, injection, blow, and compression molding; spray drying; and fiber forming and processing, including spinning, extruding, knitting, weaving, and braiding; solvent evaporation; microfluidization; emulsion processing; and the use of lasers and microfabrication techniques. These techniques may be used to fabricate virtually any form, including: films, molded objects, woven and nonwoven fabrics, fibers, laminates, impermeable and permeable barriers, dispersions, discs, pockets, reservoirs, including liquid, polymer and solid matrix reservoirs, controlled release devices, matrices, porous structures, microspheres, nanoparticles, microcapsules, pellets, slabs, beads, tubes, and so forth. Representative methods for processing the materials of the invention are described in Holmes, P. A., "Biologically Produced (R)-3-hydroxyalkanoate Polymers and Copolymers," in D. C. Bassett Ed., "Developments in Crystalline Polymers," Elsevier, London, Vol. 2, 1988, pp. 1–65; U.S. Pat. No. 4,603,070 to Steel, M. L. and Norton-Berry, P.; U.S. Pat. No. 5,502,116 to Noda, I.; and, "Biopol, Properties and Processing," Zeneca Promotional Literature, 1993.

In addition to using the materials to prepare different delivery devices or bandages, they may also be used to prepare pressure sensitive adhesives. Representative methods for preparing pressure sensitive adhesives with the materials for use in flushable drug delivery systems are described in U.S. Pat. Nos. 5,614,576 and 5,753,364 to Rutherford, D. R., Hammar, J. and Babu, G. N. and references described therein, and in WO 95/02649 to Kemmish, D. J. Suitable pressure sensitive adhesives may also be derived from latex formulations of PHA polymers.

Flushable drug delivery systems can be fabricated using the methods and materials described above, and with the procedures and designs described in U.S Pat. Nos. 3,598,122; 3,598,123; 3,731,683; 3,797,494; 4,031,894; 4,201,211; 4,286,592; 4,314,557; 4,379,454; 4,435,180; 4,588,580; 4,559,222; 4,573,995; 4,588,580; 4,645,502; 4,704,282; 4,788,062; 4,816,258; 4,849,226; 4,908,027; 4,943,435; 5,814,599; 5,879,322; and, 5,919,478.

Although described herein primarily with reference to drug delivery devices, it is understood that the devices may be used primarily for protective purposes to cover a wound to protect it from water or dirt. These devices may consist solely of the polymeric materials described above, optionally including an adhesive to secure the device at the desired site. Such adhesives are known to those skilled in the art and commonly used in making adhesive bandages.

Modifications and variations of the methods and materials described herein will be obvious to those skilled in the art and are intended to come within the scope of the appended claims.

I claim:

1. A flushable drug delivery device or bandage which degrades in an aqueous environment or sewage within one year, wherein the device or bandage comprises as a structural or adhesive component a polyhydroxyalkanoate.

2. The device of claim 1 wherein the device is manufactured in a form suitable for use as a device selected from the group consisting of a transdermal delivery patch, a buccal delivery device, a vaginal delivery device, an ophthalmic delivery device.

3. The device of claim 1 wherein the polyhydroxyalkanoate forms a laminate or barrier in the device which breaks down within six to twelve months in an aqueous environment.

4. The device of claim 1 wherein the polyhydroxyalkanoate forms a woven or non-woven fibrous material which breaks down within six to twelve months in an aqueous environment.

5. The device of claim 1 comprising a biodegradable adhesive.

6. The device of claim 5 wherein the adhesive is pressure sensitive.

7. The device of claim 5 wherein the device is an adhesive bandage.

8. The device of claim 5 wherein the adhesive is compatible with a drug or active agent.

9. The device of claim 8 wherein the adhesive can be used to control the rate of release of a drug incorporated into the device.

10. The device of claim 3 wherein the polyhydroxyalkanoate forms a drug impermeable membrane.

11. The device of claim 3 wherein the polyhydoxyalkanoate comprises a drug permeable membrane.

12. The device of claim 11 wherein the membrane can control the rate of drug release from the device.

13. The device of claim 1 wherein the polyhydroxyalkanoate is a copolymer or blend with a polymer selected from the group consisting of polyesters, polyurethanes, polyorthoesters, polyanhydrides, polyvinylacetate, cellulose acetate, polycarbonate, polysaccharides, polyamino acids, polyethylene oxide, and polyvinylalcohol.

14. The device of claim 2, further comprising an electrotransport system.

15. The device of claim 14 wherein the electrotransport system can be removed prior to flushing the drug delivery component of the transdermal patch.

16. The device of claim 1 further comprising a prophylactic, therapeutic or diagnostic agent.

17. The device of claim 16 wherein the agent is selected from the group consisting of proteins and peptides, sugars and polysaccharides, nucleic acid molecules, and synthetic drugs.

18. A method for drug delivery or to protect a wound comprising providing to a patient in need thereof a flushable drug delivery device or bandage which degrades in an aqueous environment or sewage within one year, wherein the device or bandage comprises as a structural or adhesive component a polyhydroxyalkanoate.

19. The method of claim 18 wherein the device is manufactured in a form suitable for use as a device selected from the group consisting of a transdermal delivery patch, a buccal delivery device, a vaginal delivery device, and an ophthalmic delivery device.

20. The method of claim 18 wherein the polyhydroxyalkanoate forms a laminate or barrier in the device which breaks down within six to twelve months in an aqueous environment.

21. The method of claim 18 wherein the polyhydroxyalkanoate forms a woven or non-woven fibrous material which breaks down within six to twelve months in an aqueous environment.

22. The method of claim 18 wherein the device is an adhesive bandage.

23. The method of claim 18 wherein the adhesive can be used to control the rate of release of a drug incorporated into the device.

24. The method of claim 20 wherein the polyhydroxyalkanoate forms a drug impermeable membrane.

25. The method of claim 20 wherein the polyhydoxyalkanoate comprises a drug permeable membrane, that can be used to control the rate of drug release from the device.

26. The method of claim 1 wherein the polyhydroxyalkanoate is a copolymer or blend with a polymer selected from the group consisting of polyesters, polyurethanes, polyorthoesters, polyanhydrides, polyvinylacetate, cellulose acetate, polycarbonate, polysaccharides, polyamino acids, polyethylene oxide, and polyvinylalcohol.

27. The method of claim 18, wherein the device is applied for drug delivery and comprises an electrotransport system that can be removed prior to flushing the drug delivery component of the transdermal patch.

28. The method of claim 18 further comprising administering in the device a prophylactic, therapeutic or diagnostic agent.

\* \* \* \* \*